(12) United States Patent
Myrick et al.

(10) Patent No.: US 8,345,251 B2
(45) Date of Patent: Jan. 1, 2013

(54) THIN-LAYER POROUS OPTICAL SENSORS FOR GASES AND OTHER FLUIDS

(75) Inventors: Michael L. Myrick, Irmo, SC (US); Paul G. Miney, County Leitrim (IE); Maria V. Schiza, Lancaster, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 139 days.

(21) Appl. No.: 13/026,552

(22) Filed: Feb. 14, 2011

(65) Prior Publication Data

US 2011/0199610 A1    Aug. 18, 2011

Related U.S. Application Data

(63) Continuation of application No. 10/581,407, filed as application No. PCT/US2004/043742 on Dec. 23, 2004, now Pat. No. 7,889,346.

(60) Provisional application No. 60/533,570, filed on Dec. 31, 2003.

(51) Int. Cl.
    *G01N 21/00*      (2006.01)
    *G01N 21/55*      (2006.01)

(52) U.S. Cl. .................... 356/437; 356/445

(58) Field of Classification Search .......... None
See application file for complete search history.

(56) References Cited

U.S. PATENT DOCUMENTS

| | | | |
|---|---|---|---|
| 3,717,078 A | 2/1973 | Ogura | |
| 3,761,724 A | 9/1973 | Dennis | |
| 4,499,378 A | 2/1985 | Miyatake et al. | |
| 4,607,914 A | 8/1986 | Fienup | |
| 4,687,337 A | 8/1987 | Stewart et al. | |
| 4,704,536 A | 11/1987 | Sugiyama et al. | |
| 4,891,574 A | 1/1990 | Nagaya et al. | |
| 4,981,332 A | 1/1991 | Smith | |
| 5,071,526 A | 12/1991 | Pletcher et al. | |
| 5,090,807 A | 2/1992 | Tai | |
| 5,103,340 A | 4/1992 | Dono et al. | |
| 5,137,364 A | 8/1992 | McCarthy | |
| 5,150,236 A | 9/1992 | Patel | |
| 5,223,715 A | 6/1993 | Taylor | |

(Continued)

FOREIGN PATENT DOCUMENTS

EP      1969326 A1    9/2008

(Continued)

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.

E.B. Martin et al., "Process Performance Monitoring Using Multivariate Statistical Process Control", IEE Proc.—Control Theory Appl., vol. 143, No. 2, pp. 132-144, Mar. 1996.

Mandelis et al., "Theory of Photopyroelectric Spectroscopy of Solids", Journal of Applied Physics, vol. 57, No. 9, pp. 4421-4430, 1985.

(Continued)

*Primary Examiner* — Gregory J Toatley
*Assistant Examiner* — Juan D Valentin, II
(74) *Attorney, Agent, or Firm* — Haynes and Boone, LLP

(57) ABSTRACT

A gas sensor uses optical interferents in a porous thin film cell to measure the refractive index of the pore medium. As the medium within the pores changes, spectral variations can be detected. For example, as the pores are filled with a solution, the characteristic peaks exhibit a spectral shift in one direction. Conversely, when tiny amounts of gas are produced, the peaks shift in the opposite direction. This can be used to measure gas evolution, humidity and for applications for other interferometric-based sensing devices.

13 Claims, 10 Drawing Sheets

U.S. PATENT DOCUMENTS

| | | | |
|---|---|---|---|
| 5,259,381 A | 11/1993 | Cheung et al. |
| 5,406,082 A | 4/1995 | Pearson et al. |
| 5,504,332 A | 4/1996 | Richmond et al. |
| 5,622,868 A | 4/1997 | Clarke et al. |
| 5,641,962 A | 6/1997 | Perry et al. |
| 5,710,655 A | 1/1998 | Rumbaugh et al. |
| 5,734,098 A | 3/1998 | Kraus et al. |
| 5,737,076 A | 4/1998 | Glaus et al. |
| 5,760,399 A | 6/1998 | Trygstad |
| 5,781,289 A | 7/1998 | Sabsabi et al. |
| 5,799,231 A | 8/1998 | Gates et al. |
| 5,831,742 A | 11/1998 | Watson et al. |
| 5,905,571 A | 5/1999 | Butler et al. |
| 5,939,717 A | 8/1999 | Mullins |
| 5,941,821 A | 8/1999 | Chou |
| 5,945,676 A | 8/1999 | Khalil et al. |
| 5,946,088 A | 8/1999 | Aldridge |
| 5,946,089 A | 8/1999 | Duer |
| 5,991,048 A | 11/1999 | Karlson et al. |
| 6,006,585 A | 12/1999 | Forster |
| 6,040,914 A | 3/2000 | Bortz et al. |
| 6,124,937 A | 9/2000 | Mittenzwey et al. |
| 6,137,108 A | 10/2000 | DeThomas et al. |
| 6,176,323 B1 | 1/2001 | Weirich et al. |
| 6,198,531 B1 | 3/2001 | Myrick et al. |
| 6,304,854 B1 | 10/2001 | Harris |
| 6,317,648 B1 | 11/2001 | Sleep et al. |
| 6,347,131 B1 | 2/2002 | Gusterson |
| 6,350,389 B1 | 2/2002 | Fujishima et al. |
| 6,420,708 B2 | 7/2002 | Wilks, Jr. et al. |
| 6,430,513 B1 | 8/2002 | Wang et al. |
| 6,437,326 B1 | 8/2002 | Yamate et al. |
| 6,469,785 B1 | 10/2002 | Duveneck et al. |
| 6,476,384 B1 | 11/2002 | Mullins et al. |
| 6,490,035 B1 | 12/2002 | Folestad et al. |
| 6,517,230 B1 | 2/2003 | Afnan et al. |
| 6,522,945 B2 | 2/2003 | Sleep et al. |
| 6,529,276 B1 | 3/2003 | Myrick |
| 6,573,999 B1 | 6/2003 | Yang |
| 6,600,560 B2 | 7/2003 | Mikkelsen et al. |
| 6,630,663 B2 | 10/2003 | Murphy et al. |
| 6,667,802 B2 | 12/2003 | Faus et al. |
| 6,690,464 B1 | 2/2004 | Lewis et al. |
| 6,697,195 B2 | 2/2004 | Weber et al. |
| 6,707,043 B2 | 3/2004 | Coates et al. |
| 6,711,503 B2 | 3/2004 | Haaland |
| 6,737,654 B2 | 5/2004 | Ducourant |
| 6,741,335 B2 | 5/2004 | Kinrot et al. |
| 6,748,334 B1 | 6/2004 | Perez et al. |
| 6,765,212 B2 | 7/2004 | Goetz et al. |
| 6,771,369 B2 | 8/2004 | Rzasa et al. |
| 6,776,517 B2 | 8/2004 | Afnan et al. |
| 6,798,518 B2 | 9/2004 | Difoggio et al. |
| 6,853,447 B2 | 2/2005 | Goetz |
| 6,870,629 B1 | 3/2005 | Vogel et al. |
| 6,952,267 B2 | 10/2005 | Rarac |
| 6,980,285 B1 | 12/2005 | Hansen |
| 6,982,431 B2 | 1/2006 | Modlin et al. |
| 6,995,840 B2 | 2/2006 | Hagler |
| 7,006,214 B2 | 2/2006 | Rzasa et al. |
| 7,123,844 B2 | 10/2006 | Myrick |
| 7,138,156 B1 | 11/2006 | Myrick et al. |
| 7,145,145 B2 | 12/2006 | Benson |
| 7,173,239 B2 | 2/2007 | DiFoggio |
| 7,245,374 B2 | 7/2007 | Hendriks |
| 7,271,883 B2 | 9/2007 | Newell et al. |
| 7,399,968 B2 | 7/2008 | Lewis et al. |
| 7,405,825 B2 | 7/2008 | Schuurmans et al. |
| 7,411,729 B2 | 8/2008 | Lyama et al. |
| 7,569,354 B2 | 8/2009 | Okano et al. |
| 7,623,233 B2 | 11/2009 | Freese et al. |
| 7,652,767 B2 | 1/2010 | Harsh et al. |
| 7,671,973 B2 | 3/2010 | Van Beek et al. |
| 7,697,141 B2 | 4/2010 | Jones et al. |
| 7,853,104 B2 | 12/2010 | Oota et al. |
| 7,889,346 B2 | 2/2011 | Myrick et al. |
| 7,911,605 B2 | 3/2011 | Myrick et al. |
| 7,920,258 B2 | 4/2011 | Myrick et al. |
| 2001/0034064 A1 | 10/2001 | Turner et al. |
| 2002/0008215 A1 | 1/2002 | Evans |
| 2002/0050567 A1 | 5/2002 | Boudet et al. |
| 2002/0071118 A1 | 6/2002 | Shinbori et al. |
| 2002/0108892 A1 | 8/2002 | Goetz et al. |
| 2002/0109094 A1 | 8/2002 | Goetz et al. |
| 2002/0154315 A1 | 10/2002 | Myrick |
| 2003/0056581 A1 | 3/2003 | Turner et al. |
| 2003/0059820 A1 | 3/2003 | Vo-Dinh |
| 2003/0071988 A1 | 4/2003 | Smith et al. |
| 2003/0094495 A1 | 5/2003 | Knowles et al. |
| 2003/0111606 A1 | 6/2003 | Berghmans et al. |
| 2003/0117628 A1 | 6/2003 | Harju et al. |
| 2003/0202179 A1 | 10/2003 | Larsen et al. |
| 2004/0012782 A1 | 1/2004 | Mason et al. |
| 2004/0106098 A1 | 6/2004 | Chen et al. |
| 2004/0160601 A1 | 8/2004 | Womble et al. |
| 2004/0227086 A1 | 11/2004 | Haug et al. |
| 2005/0032235 A1 | 2/2005 | Tummala et al. |
| 2005/0077476 A1 | 4/2005 | Poteet et al. |
| 2005/0087132 A1 | 4/2005 | Dickey et al. |
| 2005/0167264 A1 | 8/2005 | Sternbergh et al. |
| 2005/0251289 A1 | 11/2005 | Bonney et al. |
| 2005/0264815 A1 | 12/2005 | Wechsler et al. |
| 2005/0288906 A1 | 12/2005 | Drennen, III et al. |
| 2006/0051036 A1 | 3/2006 | Treado et al. |
| 2006/0093523 A1 | 5/2006 | Norman |
| 2006/0142955 A1 | 6/2006 | Jones et al. |
| 2006/0153492 A1 | 7/2006 | Treves et al. |
| 2006/0158734 A1 | 7/2006 | Schuurmans et al. |
| 2006/0197015 A1 | 9/2006 | Sterling et al. |
| 2006/0276697 A1 | 12/2006 | Demuth et al. |
| 2007/0035737 A1 | 2/2007 | Andrews et al. |
| 2007/0137292 A1 | 6/2007 | Xian et al. |
| 2007/0201136 A1 | 8/2007 | Myrick |
| 2007/0282647 A1 | 12/2007 | Freese et al. |
| 2007/0294094 A1 | 12/2007 | Alessandrini et al. |
| 2008/0111064 A1 | 5/2008 | Andrews et al. |
| 2008/0231849 A1 | 9/2008 | Myrick |
| 2008/0276687 A1 | 11/2008 | Myrick et al. |
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick |
| 2009/0073433 A1 | 3/2009 | Myrick et al. |
| 2009/0097024 A1 | 4/2009 | Blackburn et al. |
| 2009/0140144 A1 | 6/2009 | Myrick et al. |
| 2009/0216504 A1 | 8/2009 | Priore et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0042348 A1 | 2/2010 | Bakker |
| 2010/0073666 A1 | 3/2010 | Perkins et al. |
| 2010/0141952 A1 | 6/2010 | Myrick et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0211329 A1 | 8/2010 | Farquharson et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0305741 A1 | 12/2010 | Myrick |
| 2010/0328669 A1 | 12/2010 | Myrick et al. |

FOREIGN PATENT DOCUMENTS

| | | |
|---|---|---|
| EP | 1974201 A1 | 10/2008 |
| EP | 2087328 A2 | 8/2009 |
| EP | 2140238 A1 | 1/2010 |
| JP | 57142546 A | 9/1982 |
| WO | 2004/057284 A1 | 7/2004 |
| WO | 2005/062006 A1 | 7/2005 |
| WO | 2005/062986 A2 | 7/2005 |
| WO | 2006/031733 A2 | 3/2006 |
| WO | 2006/064446 A1 | 6/2006 |
| WO | 2006/137902 A2 | 12/2006 |
| WO | 2007/061435 A1 | 5/2007 |

| WO | 2007/061436 A1 | 5/2007 |
| WO | 2007/061437 A1 | 5/2007 |
| WO | 2007/062202 A1 | 5/2007 |
| WO | 2007/062224 A1 | 5/2007 |
| WO | 2007/064578 A2 | 6/2007 |
| WO | 2008/002903 A2 | 1/2008 |
| WO | 2008/057912 A2 | 5/2008 |
| WO | 2008/057913 A2 | 5/2008 |
| WO | 2008/121684 A1 | 10/2008 |

OTHER PUBLICATIONS

Zagonel et al., "Multivariate Monitoring of Soybean Oil Ethanolysis by FTIR", Talanta, vol. 63, No. 4, pp. 1021-1025, 2004.
Inon et al., "Combination of Mid- and Near-Infrared Spectroscopy for the Determination of the Quality Properties of Beers", Analytica Chimica Acta, vol. 571, No. 2, pp. 167-174, 2006.
Czarnik-Matusewicz et al., Temperature-Dependent Water Structural Transitions Examined by Near-IR and Mid-IR Spectra Analyzed by Multivariate Curve Resolution and Two-Dimensional Correlation Spectroscopy, Analytica Chimica Acta, vol. 544, No. 1-2, pp. 15-25, 2005.
Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.
Ghesti et al., "Application of Raman Spectroscopy to Monitor and Quantify Ethyl Esters in Soybean Oil Transesterification", Journal of the American Oil Chemists' Society, vol. 83, pp. 597-601, 2006.
Dereniak et al., *Infrared Detectors and Systems*, John Wiley & Sons: New York, Chapter 9, pp. 395-438, 1996.
Prystay et al., "Thermophysical Measurements and Interfacial Adhesion Studies in Ultrathin Polymer Films Using Homodyne Photothermal Spectrometry", Applied Spectroscopy, vol. 47, No. 4, pp. 501-514, 1993.
Simcock et al, "Tuning D* with Modified Thermal Detectors", Applied Spectroscopy, vol. 60, No. 12, pp. 1469-1476, 2006.
Lang, "Ferroelectric Polymers and Ceramic-Polymer Composites", Key Engineering Materials, vol. 92-93, pp. 83-142, 1994.
Profeta et al., "Spectral Resolution in Multivariate Optical Computing", Spectrochimica Acta Part A: Molecular and Biomolecular Spectroscopy, vol. 67, pp. 483-502, 2007.
Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.
Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.
Knothe, "Analyzing Biodiesel: Standards and Other Methods", Journal of the American Oil Chemists Society, vol. 83, No. 10, pp. 823-833, 2006.
E.D. Palik, *Handbook of Optical Constants of Solids I*, Academic Press, San Diego, pp. 350-357, 1998.
M.L. Myrick, "Multivariate optical elements simplify spectroscopy", Laser Focus World 38, 91-94, 2002.
O. Soyemi et al., "Design and testing of a multivariate optical element: The first demonstration of multivariate optical computing for predictive spectroscopy", Anal. Chem. 73, No. 6, pp. 1069-1079, (2001).
M.L. Myrick et al., "A single-element all-optical approach to chemometric prediction", Vib. Spectrosc. 28, 73-81, 2002.
A.M.C. Prakash et al., "Optical regression: a method for improving quantitative precision of multivariate prediction with single channel spectrometers", Chemom. Intell. Lab. Syst. 46, 265-274, 1999.
R.A. Deverse et al., "Realization of the Hadamard multiplex advantage using a programmable optical mask in a dispersive flat-field near-infrared spectrometer", Appl. Spectrosc. 54, 1751-1758, 2000.
F.G. Haibach et al., "Precision in multivariate optical computing", Appl. Optics 43, 2130-2140, 2004.
M.L. Myrick et al., "Application of multivariate optical computing to simple near-infrared point measurements", Proceedings of the SPIE, Bellingham, VA, US, vol. 4574, pp. 208-215, 2002.
O.S. Heavens, *Optical Properties of Thin Solid Films*, Dover Publications, Inc., Mineola, USA, pp. 62-81, 242-249, 1991.
S. Betancourt et al., "Analyzing Hydrocarbons in the Borehole", Oilfield Review, pp. 54-61, Autumn 2003.
D. Eastvvood et al., "Field applications of stand-off sensing using visible/NIR multivariate optical computing", Ground and Air Pollution Monitoring and Remediation, SPIE vol. 4199, pp. 105-114, 2001.
Haibach et al., "On-line Reoptimization of Filter Designs for Multivariate Optical Elements", Applied Optics, vol. 42, No. 10, pp. 1833-1838, Apr. 1, 2003.
Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.
M.P. Nelson et al., "Multivariate optical computation for predictive spectroscopy", SPIE Vo. 3261, pp. 232-243, 1998.
O. Soyemi et al., "A Simple Optical Computing Device for Chemical Analysis", Proceedings of SPIE Vo. 4284, pp. 17-28, 2001.
O. Soyemi et al., "Design of angle tolerant multivariate optical elements for chemical imaging", Applied Optics, vol. 41, No. 10, pp. 1936-1941, Apr. 1, 2002.
O. Soyemi et al., "Nonlinear Optimization Algorithm for Multivariate Optical Element Design", Applied Spectroscopy, vol. 56, No. 4, pp. 477-487, 2002.
O. Soyemi et al., "Novel Filter Design Algorithm for Multivariate Optical Computing", Advanced Environmental and Chemical Sensing Technology, Proceedings of SPIE Vo. 4205, pp. 288-299, 2001.
Strausz et al., "About the Colloidal Nature of Asphaltenes and the MW of Covalent Monomeric Units", American Chemical Society, Energy and Fuels 16, No. 4, pp. 809-822, 2002 (abstract).
N. Aske et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 1304-1312, 2001.
N. Aske et al., "Asphaltene Aggregation from Crude Oils and Models Systems Studied by High-Pressure NIR Spectroscopy", Energy and Fuels, American Chemical Society, 16, No. 5, pp. 1287-1295, 2002.
Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.
Y. Yan et al. "Fluorescence Fingerprint of Waters: Excitation-Emission Matrix Spectroscopy as a Tracking Tool", Applied Spectroscopy, vol. 54, No. 10, pp. 1539-1542, 2000.
M.P. Nelson et al., "Multivariate optical computation for predictive spectroscopy", Analytical Chemistry, vol. 70, No. 1, pp. 73-82, Jan. 1, 1998.
M.P. Nelson et al., "Fabrication and evaluation of a dimension-reduction fiberoptic system for chemical imaging applications", Review of Scientific Instruments, vol. 70, No. 6, pp. 2836-2843, Jun. 1999.
M.L. Myrick, "New approaches to implementing predictive spectroscopy", Proceedings of the SPIE Conference on Pattern Recognition, Chemometrics, and Imaging for Optical Environmental Monitoring, SPIE vol. 3854, pp. 98-102, Sep. 1999.
M. Groner et al., "Identification of Major Water-Soluble Fluorescent Components of Some Petrochemicals", Marine Pollution Bulletin, vol. 42, No. 10, pp. 935-941, 2001.
M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.
M.L. Myrick et al., "Spectral tolerance determination for multivariate optical element design", Fresenius J Anal Chem, 369:351-355, 2001.
R.J. Priore et al., "Miniature Stereo Spectral Imaging System for Multivariate Optical Computing", Applied Spectroscopy, vol. 58, No. 7, pp. 870-873, 2004.
M.L. Myrick et al., "Use of Molecular Symmetry to Describe Pauli Principle Effects on the Vibration-Rotation Spectroscopy of $CO_2(g)$", Journal of Chemical Education, vol. 81, No. 3, pp. 379-382, Mar. 2004.
M.N. Simcock et al., "Precision in imaging multivariate optical computing", Applied Optics, vol. 46., No. 7, pp. 1066-1080, Mar. 1, 2007.

Ozturk et al., "Filtering Characteristics of Hybrid Integrated Polymer and Compound Semiconductor Waveguides", In: Journal of Lightwave Technology, vol. 20, No. 8, pp. 1530-1536, Aug. 2002.

P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.

Mullins et al., "Gas-Oil Ratio of Live Crude Oils Determined by Near-Infrared Spectroscopy", Applied Spectroscopy, vol. 55, No. 2, pp. 197-201, 2001.

THIN-LAYER POROUS OPTICAL SENSORS FOR GASES AND OTHER FLUIDS

CROSS-REFERENCE TO RELATED APPLICATIONS

The present application is a continuation of U.S. application Ser. No. 10/581,407 filed Jun. 6, 2008 now U.S. Pat. No. 7,889,346; which was a U.S. National-Stage Application (under 35 U.S.C. §371) of PCT International Application No. PCT/US2004/043742, filed Dec. 23, 2004; which claims priority to U.S. Provisional Application No. 60/533,570, filed Dec. 31, 2003. The entire contents of each of these applications is specifically incorporated herein in its entirety by express reference thereto.

STATEMENT OF FEDERALLY SPONSORED RESEARCH OR DEVELOPMENT

Research described in this application was sponsored by the Human Effectiveness Directorate, Air Force Research Laboratory, Air Force Materiel Command, United States Air Force, under grant number F33615-00-2-6059.

FIELD OF THE INVENTION

The present invention relates to a thin layer electrode and methodologies for taking spectroscopic or interferometric measurements of a fluid. In particular, the presently disclosed technology relates to an optically reflective thin layer electrode (ORTLE) for, e.g., spectroscopic interrogation of a solution phase within channels or pores of a film in the ORTLE.

BACKGROUND OF THE INVENTION

Since first reported in 1967, optically transparent thin layer electrodes (OTTLEs) have been used for thin layer studies. Spectroelectrochemistry, for example, is a combination of electrochemical and spectroscopic techniques in which optical measurements are referred to the potential of a working electrode. Thin-layer spectroelectrochemistry is possibly the simplest type of spectroelectrochemistry and has advantages such as rapid and exhaustive electrolysis and small volume features. A typical application of an OTTLE is the spectroscopic study of "redox" processes; i.e., reactions in which the acceptance of an electron (reduction) by a material is matched with the donation of an electron (oxidation). Various spectroscopic techniques such as luminescence spectroscopy, Fourier transform infrared (FTIR) difference spectroscopy and ultraviolet/visible/near infrared (UV/vis/NIR) have been coupled with electrochemical techniques via OTTLEs. A variety of OTTLE designs for many purposes have been developed, and all generally operate on transmittance principles.

BRIEF SUMMARY OF THE INVENTION

The present invention is directed to spectroelectrochemical, spectroscopic and/or interferometric analyses of a material trapped in pores of a thin layer film. More specifically, the invention is directed to an optically reflective thin layer electrode (ORTLE) that operates on reflectance principles; i.e., the ORTLE collects reflectance rather than facilitating transmittance through a fluid. As used herein, the term fluid is used to mean a continuous amorphous medium, matter or substance—e.g., a liquid, including a solution, or a gas—that tends to flow and to conform to an outline of its container and will not destroy the thin layer film.

The ORTLE is fabricated, for instance, by anodizing a thin layer of aluminum sputtered onto a glass substrate, such as a float glass microscope slide, to create a 250 nm to 1000 nm-thick, porous, aluminum oxide (alumina) film. The resulting alumina film is transparent and contains channels or pores that vary from approximately 80 to 100 nm in diameter with depths of approximately 250 nm to 1000 nm. The thickness of the alumina film—and thus the depth of the pores—can be altered by controlling the thickness of the original aluminum film. Although alumina is provided by way of an enabling example, any porous membrane with channels or pores to trap the fluid for spectroscopic, interferometric, or spectroelectrochemical measurements can be used to practice the invention.

In one aspect of the invention, a thin film of gold is sputtered atop the alumina film. The gold layer adheres to surface points of the alumina film such that the gold layer remains porous to allow a solution into the pores of the alumina film while remaining optically thick and reflective. The gold layer is filled with holes each having a diameter substantially less than the wavelength of visible light. As discussed below, the gold layer can serve as an electrode but is not limited to such use. Furthermore, other metals and materials with reflective properties can be substituted for gold and thus used to practice the invention.

As described in detail herein, the ORTLE interrogates a very thin film sample based on porous alumina. Through the use of a combination of specular reflectance spectroscopy and chronoamperometry, the spectroelectrochemical study is confined to that solution contained within the pores of the ORTLE. Specifically, spectroscopy interrogates a solution phase within the pores of the alumina film between the electrode face and a window behind it. Reflectance measurements are thus made through the glass slide but do not interrogate a surrounding bulk solution.

According to exemplary experiments described herein, the reflectance measurements show spectral features that shift with the optical properties of the material filling the pores of the alumina film. The stability of the ORTLE spectrum and its origin are described by examples below to show how an applied potential affects the observed spectrum in a simple solution. For instance, a series of experiments in which the potential of the ORTLE is stepped negatively to various values in an aqueous sodium sulfate solution shows that interference fringes shift measurably in the ORTLE spectrum at potentials seveial hundred millivolts positive of the potential at which gas evolution was visible to the naked eye.

According to a particular aspect of the invention, a method is provided for analyzing matter such as by interferometric, spectroscopic, and/or electrochemical and optical spectroscopic (spectroelectrochemisty) techniques. The method includes the steps of (a) introducing a liquid or gaseous matter into an optically reflective thin layer electrode, the electrode including a transparent base substrate with alumina film disposed thereon, the alumina film defining a plurality of pores therein, and a gold film disposed on the alumina film such that a quantity of the liquid or gaseous matter can enter at least one of the pores; (b) applying a potential to the gold film such that the quantity of the liquid or gaseous matter in the pores is isolated from a remaining bulk of the liquid or gaseous matter disposed about the electrode; and (c) directing light from a source into the electrode from proximate the base substrate in a direction of the gold film, the fold film under the potential configured to reflect the light into the quantity of the liquid or gaseous matter in the pores for analysis of the reflected light.

According to the method, the liquid or gaseous matter is selected from the group consisting of potassium ferricyanide, sodium sulfate, water and solutions thereof. The liquid or gaseous matter can be a solution of 0.01M ferricyanide, 0.05M sodium sulfate, and deionized water. The transparent base substrate is made of glass. The applied potential is between +0.4V to −1.5V and can be held for between about 200 seconds to about 400 seconds.

According to the method, the light can be directed at the base substrate at about a 45° angle, and may further include the step of monitoring the reflected light in the quantity of the liquid or gaseous matter isolated in the pores by reflectance spectroscopy.

According to another aspect of the invention, an optically reflective thin layer includes a transparent base substrate; a film disposed on the base substrate, the film defining a plurality of pores therein; and a reflective material disposed on the film such that the pores are exposed to atmosphere, the reflective material having a specular surface for reflection of light into the pores for taking measurements of a fluid isolated therein from the atmosphere.

In this example, the pores are from 80 to about 100 am in diameter and from 250 nm to about 1000 nm deep, more particularly about 750 nm, and hold a quantity of fluid when the optically reflective thin layer is immersed in the fluid. The fluid can be selected from ferricyanide, sodium sulfate, water, a gas, or combinations of these. More particularly, the fluid can be a solution of 0.01M ferricyanide, 0.05M sodium sulfate, and deionized water.

Also in this aspect, the gold film will reflect light transmitted from a direction of the base substrate into the quantity of fluid in the pores when a potential is applied. The quantity of fluid is monitorable by specular reflectance spectroscopy using the reflected light, or by spectroelectrochemical analysis or interferometric analysis or combinations of these methodologies. A detector arranged at about 90° to the reflected light is provided for monitoring and taking measurements.

In yet another embodiment of the present invention, a thin layer electrode includes a transparent base substrate with a porous thin film disposed on the base substrate, and a material disposed on the thin film such that the pores are exposed to atmosphere containing a fluid.

In an aspect of this embodiment, the material is a gold film, which will isolate a portion of the fluid in the pores away from a remainder of the fluid in the atmosphere when a potential is applied. The gold film is also optically reflective when the potential is applied to redirect an incident light beam into the pores as the light beam passes through the transparent base substrate into the pores in a direction of the gold film. Additionally, the gold film has a nanostructured face disposed away from the thin film, which filters scatter-causing particles suspended in the fluid.

Similar to the foregoing aspects of the invention, the transparent base substrate can be glass and the thin film can be alumina. By way of example, the thin film alumina has a depth of 250 nm to about 1000 nm and exhibits pores of about 80 nm to about 100 nm in diameter and from 250 nm to about 1000 nm deep. Also, the fluid in this aspect is a solution of ferricyanide, sodium sulfate, and water, more particularly deionized water, or a gas, or combinations of these components.

In another aspect of the invention, a thin layer apparatus for fluid analysis is provided with a transparent base substrate, and a thin film sputtered on the base substrate. The thin film has a plurality of pores, each of which has a diameter of 80 nm to about 100 nm and depths of 250 nm to about 1000 nm. Similar to the foregoing embodiments, the pores isolate a portion of a fluid from a remainder of a bulk fluid in which the thin layer apparatus is immersed.

A material can be layered on the thin film in this aspect such that the pores remain open in communication with the fluid. The material has a specular surface to reflect into the pores an incident beam entering the pores through the transparent base substrate in a direction of the material such that the isolated fluid in the pores can be analyzed by specular reflectance spectroscopy using the reflected light, or by spectroelectrochemical analysis or interferometric analysis or combinations of these methodologies.

BRIEF DESCRIPTION OF THE DRAWINGS

The above and other aspects and advantages of the present invention are apparent from the detailed description below in combination with the drawings, in which.

DETAILED DESCRIPTION OF THE INVENTION

Figure 1:
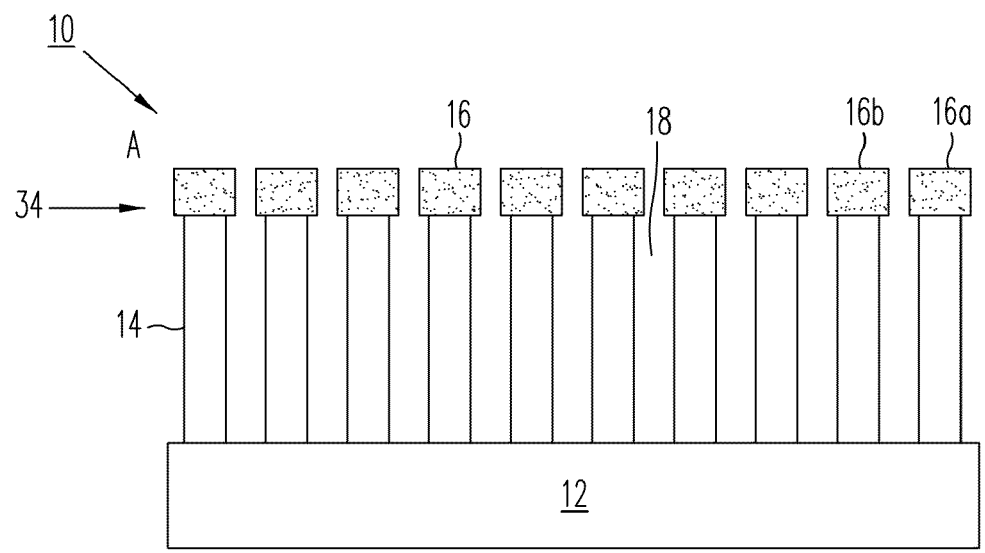
FIG. 1A is a schematic elevational view of an ORTLE according to an aspect of the present invention.
FIG. 1B is a SEM image of porous alumina covered with a layer of gold as in FIG. 1A, particularly showing unsealed pores in the porous alumina.
Figure 1:
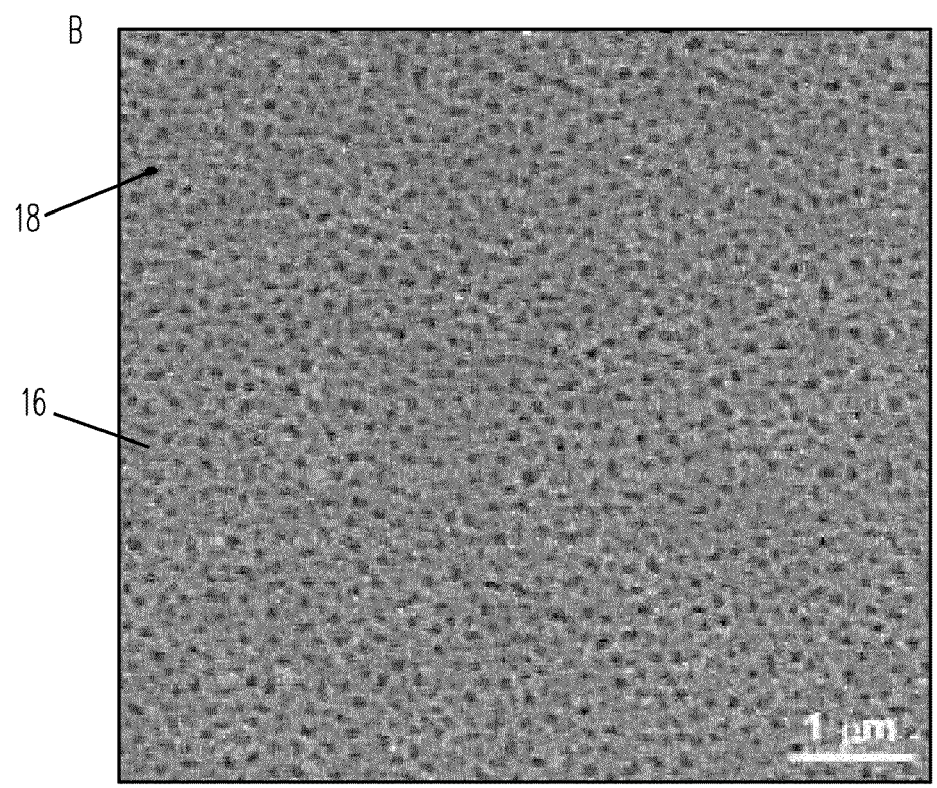

Detailed reference will now be made to the drawings in which examples embodying the present invention are shown. The detailed description uses numerical and letter designations to refer to features of the drawings. Like or similar designations of the drawings and description have been used to refer to like or similar parts of the invention.

The drawings and detailed description provide a full and detailed written description of the invention and of the manner and process of making and using it, so as to enable one skilled in the pertinent art to make and use it, as well as the best mode of carrying out the invention. However, the examples set forth in the drawings and detailed description are provided by way of explanation of the invention and are not meant as limitations of the invention. The present invention thus includes any modifications and variations of the following examples as come within the scope of the appended claims and their equivalents.

ORTLE Design and Concept

An optically reflective thin layer electrode (ORTLE) generally designated by the reference numeral 10 is broadly depicted in FIG. 1A. In this example, a 500 nm aluminum film was sputtered substantially onto a base substrate such as a transparent float glass slide 12, anodized and subsequently converted to porous alumina 14. Specifically, a 750 nm-thick, transparent, alumina film 14 results due to conversion from aluminum metal to alumina (aluminum oxide). The alumina film 14 was subsequently coated for 210 seconds with gold using a sputtering system (not shown) such as a CRC-100 sputtering system available from Plasma Sciences Inc. of Lorton, Virginia. The sputtering system produced a gold film 16 approximately 100 nm thick.

Although the film 16 appears in FIG. 1A to be an optically thick gold film, scanning electron microscopy (SEM) laboratory studies have shown it insufficient to seal the relatively larger pores of a porous alumina membrane. Specifically, a SEM image in FIG. 1B shows that channels or pores 18 of the alumina film 14 created by the above conversion process also remain open when coated with gold in the foregoing manner.

The gold film 16 possesses a mirror finish on its face 16a—the exposed side opposite the porous alumina 14. Despite this and the apparent continuity of the film 16, it is highly porous thus exposing the channels 18 in the underlying alumina 14 to atmosphere. A reverse side 16b of the gold film 16, however, does not show a highly reflective finish, although it presents a mostly specular surfade. As briefly introduced, other metals or materials exhibiting reflective qualities can be substituted for the exemplary gold film 16.

When exposed to a bulk solution S (see FIG. 2), the channels 18 are filled with a quantity or portion of the solution S. Light can pass through the optically transparent glass slide 12 used as a support and through the fluid-filled alumina 14, but is reflected by the porous metal overlayer 16. If a potential is applied to the gold film 16, any solution S changes that occur within the pores 18 can be monitored by specular reflectance spectroscopy. The ORTLE design advantageously requires no special auxiliary or reference electrodes and no special electrode configurations.

Those skilled in the art will immediately recognize and appreciate that deeper pores, e.g., greater than about 750 nm, will provide a stronger spectrum of the material in the pores 18, but will take longer to equilibrate with material outside the pores 18 since spectrum strength increases linearly with length. Conversely, shallower pores, e.g., less than about 750 nm, will equilibrate faster for faster measurements but will provide a weaker spectrum since equilibration time increases as the square of length.

Cell Design and Set-Up

Figure 2:
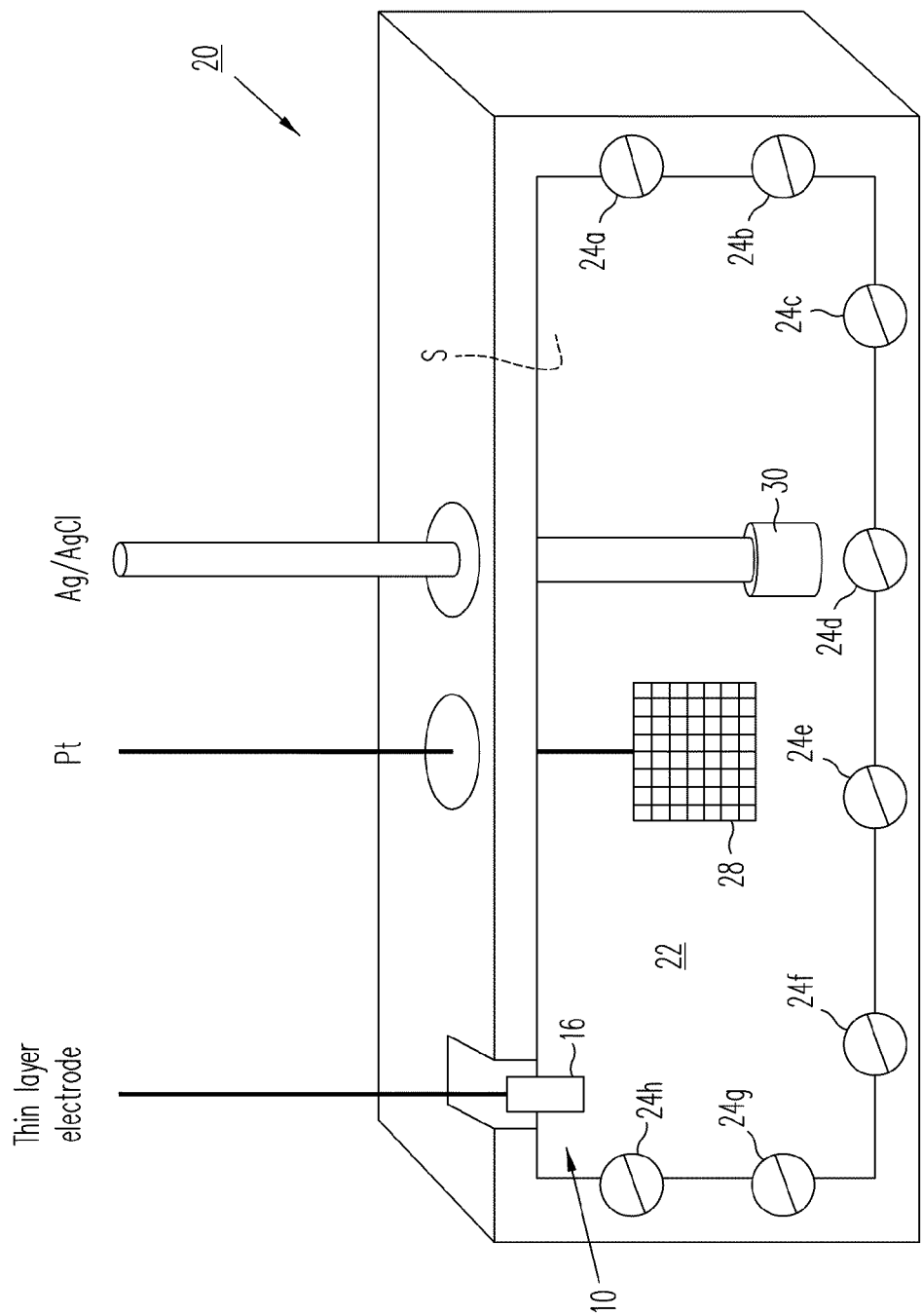
FIG. 2 is a schematic of a cell in which the ORTLE as in FIG. 1 is mounted.

The present cell design is used as a window into the bulk solution S, since only the solution S in the alumina pores 18 is interrogated. As shown in FIG. 2, the ORTLE 10 is mounted in an exemplary cell 20. The cell 20 is constructed from a Teflo®-brand material and contained in a rectangular window 22 (e.g., 75×75×0.5 mm) to which the thin layer electrode 10 is attached. The ORTLE 10 is positioned with the gold sputtered surface or side 16 facing inwards as shown and held in place, for instance, by eight screws 24a-h, which can be tightened to avoid leaking of the solution S.

As described by example operation below, the ORTLE 10 can be used in the foregoing arrangement as a working electrode in the cell 20 for spectroelectrochemical analysis. However, the skilled artisan will recognize that the ORTLE 10 need not be used an electrode nor is the arrangement limited to spectroelectrochemical analysis. For instance, the ORTLE 10 can be used for spectroscopic and interferometric analyses of material trapped in the pores 18 of the alumina 14. As presented below, while an interference pattern can shift to indicate a change in a refractive index of the material filling the pores 18, one skilled in the art can also perform infrared or UV-visible spectroscopy measurements for identification of the pore fluids. Thus, the measurements may not be purely interferometric in nature and may include absorption properties of the fluid.

Figure 3:
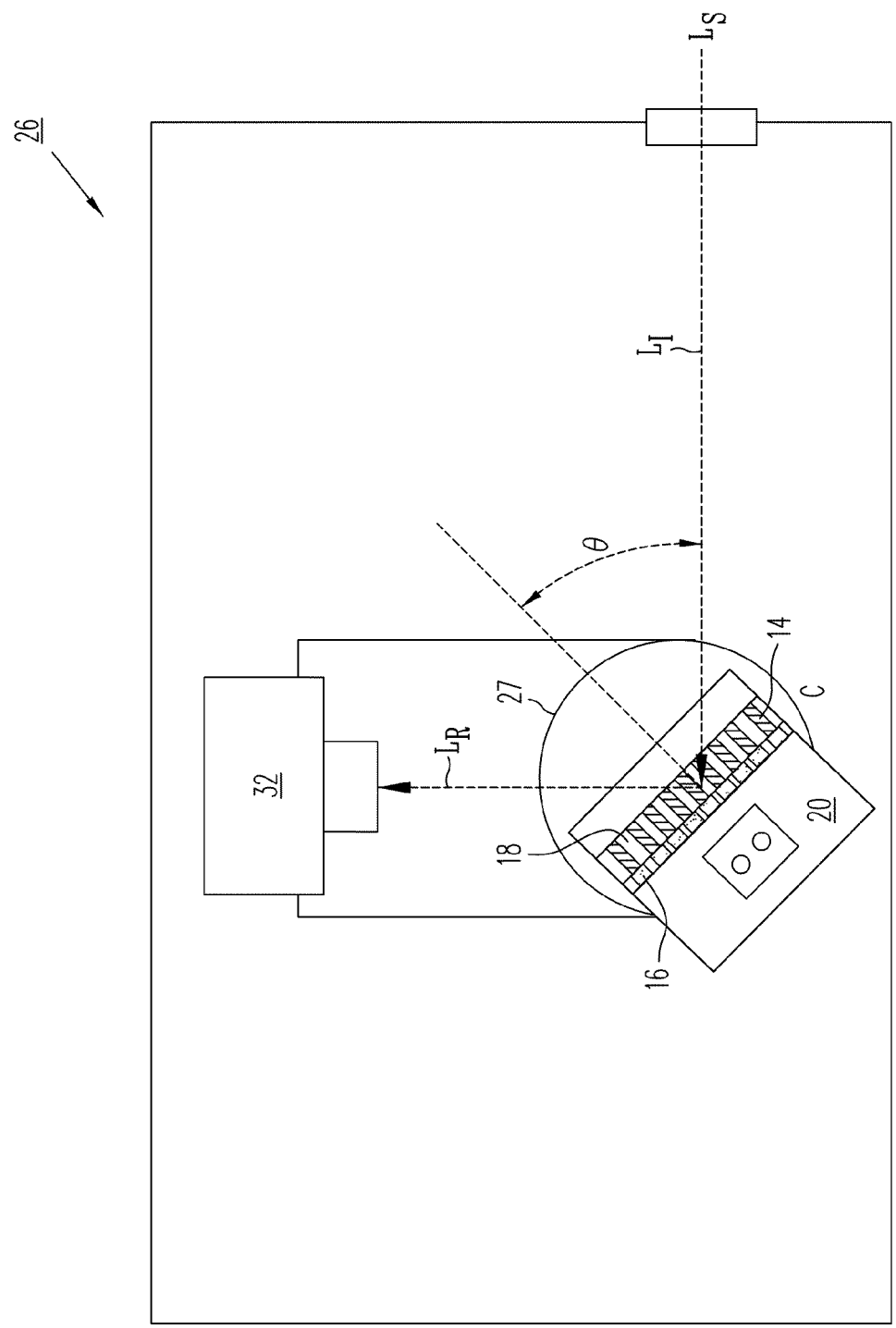
FIG. 3 is a schematic plan view of the cell as in FIG. 2.

With reference to FIGS. 2 and 3, the cell 20 is mounted on an aluminum base 27, which is placed inside a spectrometer 26. The height of this aluminum base 27 is selected to place the ORTLE 10 in a path of an incident light beam $L_I$ emanating from a light source $L_S$. With the ORTLE 10 so attached, the cell 20 is filled with the desired solution S, into which an auxiliary electrode 28 and a reference electrode 30 are inserted. In this example, the auxiliary electrode 28 is platinum (Pt) gauze and the reference electrode 30 is Ag/AgCl/sat: NaCl, available from BAS of West LaFayette, Ind. Also by way of example, an OL 750-75MA Automated Goniospectroreflectance Attachment, available from Optronic Laboratories, Inc. in Orlando, Fla., is suitable for use as the spectrometer 26.

As shown in FIG. 3, the cell 20 is illuminated by the light source $L_S$, such as a tungsten quartz-halogen lamp (150 W) and a 750 M-S Monochromator combination. This light source combination $L_S$ has selectable wavelengths in the range of 280-1100 nm. The Monochromator in this example is available from Optronic Laboratories, Inc, but may be substituted with other suitable devices.

A silicon detector 32 in FIG. 3 is used to record intensity of reflected light $L_R$. An exemplary detector is available from Optronic Laboratories, Inc. under the designation "DH-300EC, OL750-HSD-301EC". Spectra (see, e.g., FIG. 6) are obtained by appropriate software such as that available from Optronic Laboratories, Inc. The spectra are analyzed using, for example, IGOR Pro, Version 4.01, available from Wavemetrics, Inc. of Lake Oswego, Oregon.

All electrochemical experiments in the examples detailed below are carried out using an EG&G PARC Model 263 potentiostat connected with a general purpose interface bus (GPIB), available from National Instruments of Atlanta, Ga. The GPIB is connected to a Gateway 2000 Model P5-60 computer with EG&G Model 270 Research Electrochemistry Powersuite Software. Gold wire electrodes are available from CH Instruments of Austin, Tex. Potassium ferricyanide is available from Mallinckrodt of Hazelwood, Mo., and sodium sulfate is available from Fisher Scientific of Suwanee, Ga. The potassium ferricyanide and sodium sulfate are all reagent grade and are used without further purification. All solutions were prepared with deionized water. SEM images were collected using a Quanta 200 scanning electron microscope available from FEI Company of Hillsboro, Oreg.

Those skilled in the art will recognize that the foregoing equipment and materials are provided by way of example only and many suitable substitutions can be made to practice the invention as described below.

The present invention may be better understood with respect to the following examples.

EXAMPLES

With reference to the figures and for exemplary purposes only, the following methodologies and embodiments are employed for interrogation of a solution phase within pores of the film in the ORTLE 10.

Example 1

Characterization of the ORTLE

Figure 4:
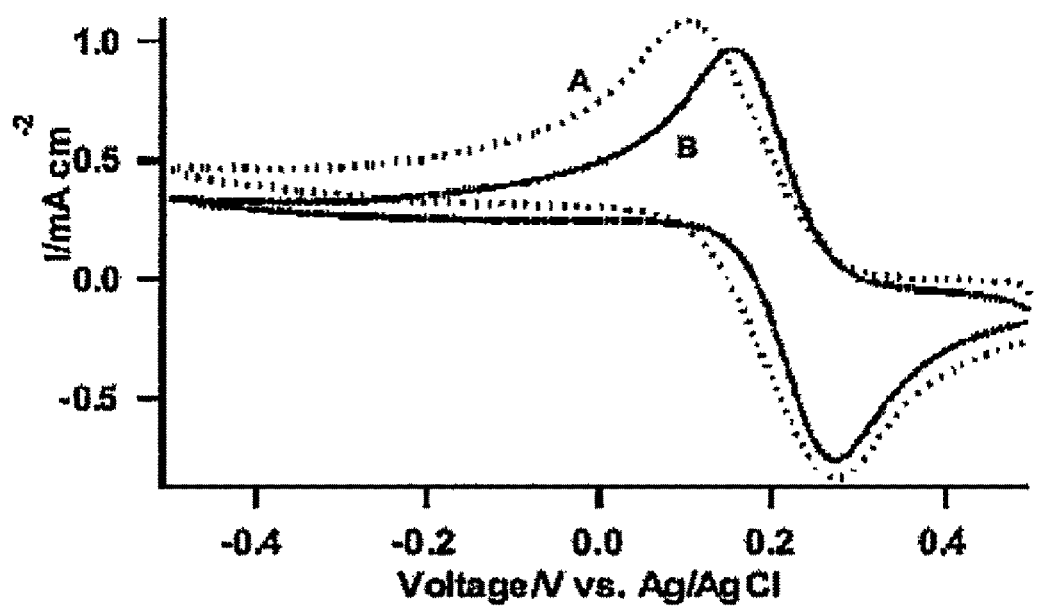
FIG. 4 is a graph showing cyclic voltammograms (CV) obtained for a standard gold electrode and the ORTLE as in FIG. 2 immersed in an electrolyte solution with a potential applied.

FIG. 4 depicts results of the ORTLE 10 used as a working electrode. As shown, a comparison is made between a cyclic voltammogram (CV) obtained at a conventional gold wire electrode (A) and one obtained using the ORTLE 10 as a working electrode (B). Both experiments were carried out in 0.01 M ferricyanide/0.05M sodium sulfate solutions at 20 mVs$^{-1}$. According to FIG. 4, the ORTLE 10 behaves similarly to the wire electrode (A). The purely electrochemical characteristics of the ORTLE electrode reflect those of bulk solution conditions because the electrode 10 is immersed in bulk solution. This experiment shows the ability of the ORTLE 10 to exhibit the standard characteristics that would be expected in a ferricyanide solution given that the design of the electrode 10 is such that the very thin gold layer 16 sputtered on the porous alumina film 14 does not seal the pores 18 as previously described.

More specifically, FIG. 4 shows a decrease in the separation of the peaks for the ORTLE 10, which would be expected for a contribution from restricted diffusion occurring within the pores 18. To test this, an experiment was conducted to measure the effect of sweep rate (v) on the peak current. For a thin layer cell, the peak current should be directly proportional to v. This experiment revealed a poor relationship between peak current and v and an excellent relationship between peak current and $v^{1/2}$ ($R^2$=0.999). The result indicates that for this CV the contribution of thin layer electrochemistry is negligible compared to that of the bulk solution.

Figure 5:
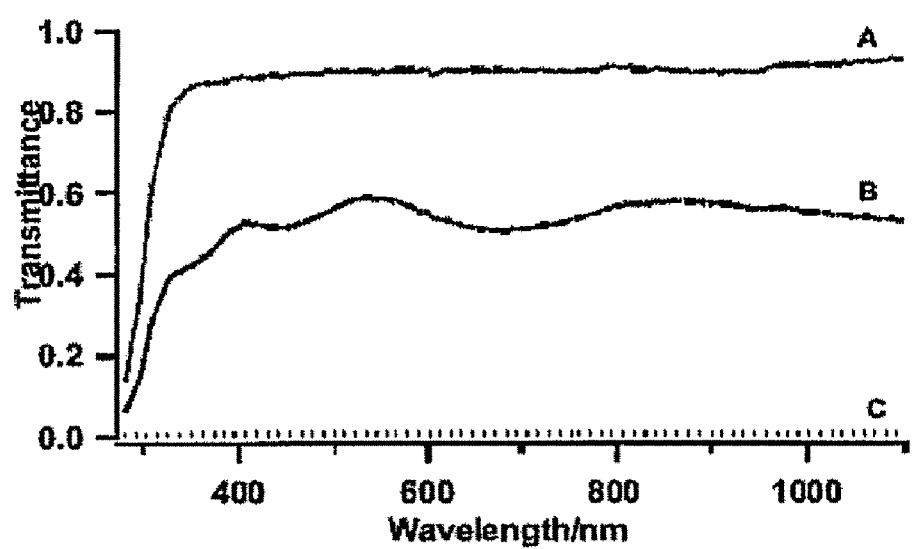
FIG. 5 is a graph showing transmission spectra for a glass slide, a glass slide coated with an alumina layer, and the ORTLE as in FIG. 1.

Turning to FIG. 5, a plot shows transmitting spectra of a plain float glass microscope slide (A), of a similar glass slide with a layer of porous alumina (B), and of an ORTLE (C), all taken at an angle θ, e.g., about 45°, to an incident beam (see, e.g., $L_I$ in FIG. 3). Interference effects in the spectrum (B) are the result of the refractive index contract between glass and the overlying films, while the reduced overall transmittance of the ORTLE is negligible on the scale of FIG. 5 due to the presence of the reflective gold film and thus little interrogation of the bulk solution can occur through the film. Spectroscopic changes based on specular reflectance on the backside of the gold film must therefore be ascribed to either changes in the medium within the pores or changes in the electrode itself.

Figure 6:
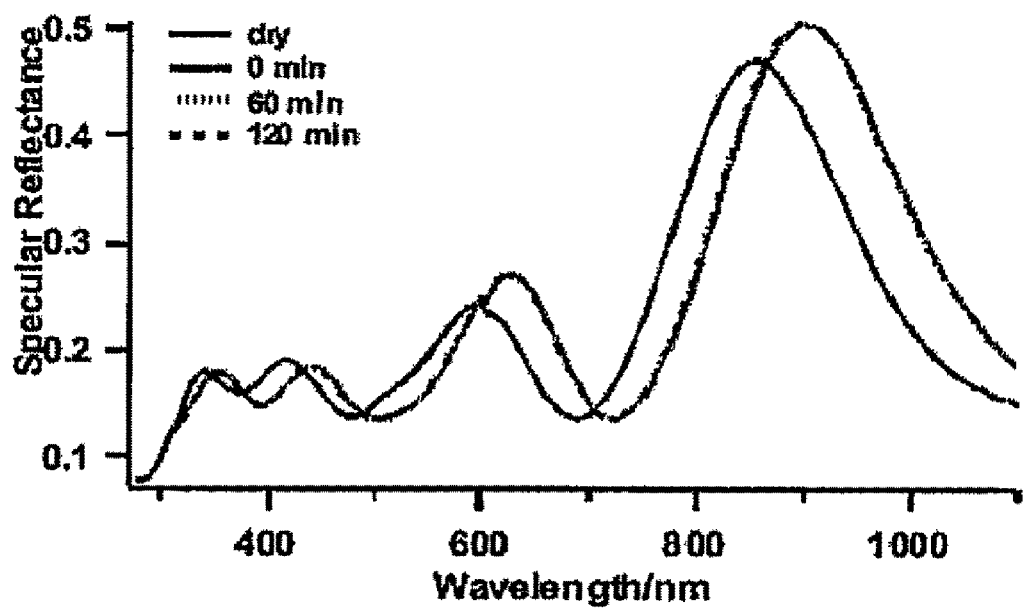
FIG. 6 is a graph showing specular reflectance spectra including a red shift observed after introduction of a 0.05M sodium sulfate solution and changes in the spectra over time.

FIG. 6 shows a typical specular reflectance spectrum (solid black line) obtained for the ORTLE 10 without any solution in the cell (see, e.g., cell 20 in FIG. 2). The specular reflectance measurements were performed by positioning the cell at angle θ, e.g., about 25° to 75°, more particularly 45°, to the incident beam $L_I$, and the detector 32 at about 80° to 95°, more particularly 90°, to the specular reflected beam (see FIG. 3). By positioning the cell 20 and the detector 32 at relatively steeper angles, pathlength and sensitivity of the reflected beam are increased. Further, steeper angles introduce polarization effects that can be used for internal calibration of the components.

With continued reference to FIG. 6, single-beam reflectance measurements were referenced to the total intensity of the source by directing 100% of the incident beam to the detector before each experiment. Several small interference peaks can be observed at shorter wavelengths with a relatively large peak usually observed within the range of approximately 700-1000 nm (the wavelengths and the appearance of the peaks varied from ORTLE to ORTLE due to slight differences in the thickness of the original aluminum films). Upon the introduction of a sodium sulfate solution, the peaks shifted towards longer wavelengths, accompanied by an increase in intensity—for this sample the large peak shifted from 850 to 900 nm, as indicated by the spectrum collected after 0 min (i.e., it was collected immediately after the introduction of the sodium sulfate solution). The spectra collected after 60 min and 120 min show that for this ORTLE no further red shifts or increases in intensity were observed. While this particular ORTLE responded promptly, some ORTLEs showed a gradual red shift over time after solution was introduced. In all cases, less than 1 hour was necessary for this change to be completed. At least part of this change is likely the result of pores being filled with solution and changing the effective refractive index of the porous film, as the shift is consistent with changes in interference fringe positions expected in that case within a factor of two.

Figure 7:
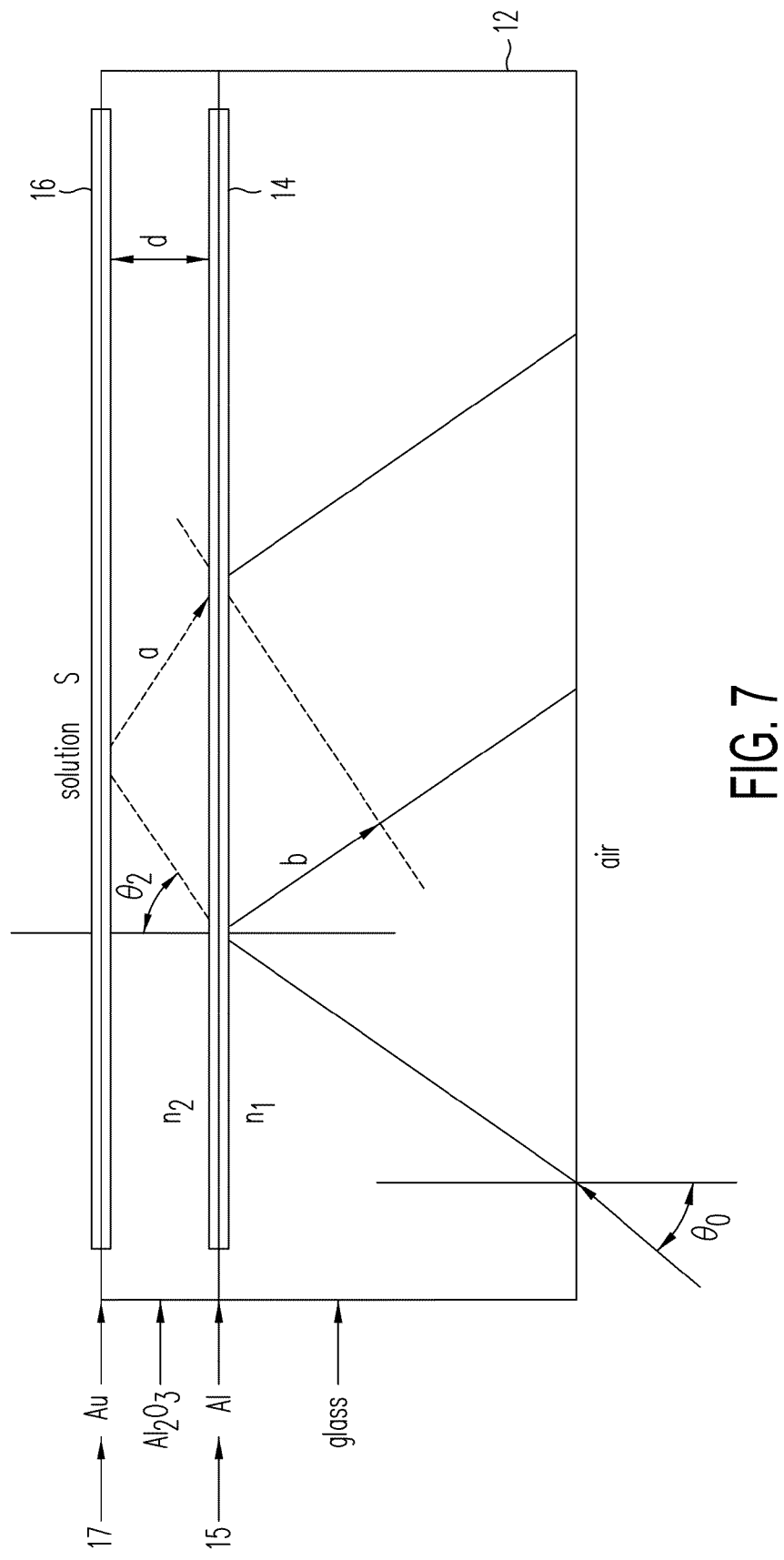
FIG. 7 is a schematic plan view of optical path-lengths of incident light from air through a glass substrate and alumina layer with two reflective interfaces resulting from unanodized aluminum and gold coating.

Referring now to FIG. 7, one condition for the appearance of strong interference-based oscillations in the reflection spectrum of the ORTLE 10 is that the reflectivity of a glass/alumina interface 15 and an alumina/gold interface 17 are of comparable magnitudes. This is achieved only because the electrochemical synthesis of the porous alumina film 14 leaves a small amount of aluminum metal behind at the glass/alumina interface 15, approximately 1.2 nm thickness on average as indicated by ellipsometry. Aluminum is the most opaque metal in the visible region. According to optical modeling of this electrode, too much aluminum at the interfaces 15, 17 (e.g., 50 nm) would cause the spectrum of the ORTLE 10 to be that of an aluminum mirror. Too little aluminum at the interfaces 15, 17 would produce a spectrum like that of a gold mirror with small (e.g., 5%) interference oscillations in the blue and ultraviolet, dropping to about 1% oscillation in the red and near infrared.

With this first condition met, constructive interference in reflection occurs when the difference in the optical pathlengths a and b are an integral number of wavelengths of incident light. Assuming an isotropic material with no absorbance, the optical pathlength is the physical pathlength multiplied by the (real) refractive index of the medium. Making use of Snell's law:

$$\sin(\theta_0)=n_1 \sin(\theta_1)=n_2 \sin(\theta_2)$$

where $\theta_0$ is the angle of the incident light $L_I$ from air to the glass substrate 12, $\theta_1$ is the angle that the beam enters the porous alumina layer 14 from the glass substrate 12, $\theta_2$ is the angle of the beam that interacts with the gold layer 16 and $n_1$ and $n_2$ are refractive indices of the glass 12 and porous alumina layer 14, respectively.

It is possible to show that the optical path difference (OPD) is:

$$OPD=2d\sqrt{n_2^2-\sin^2(\theta_0)}=m\lambda_{max},$$

where m is a non-negative integer, d is the film thickness and $\lambda_{max}$ is the maximum wavelength. The apparent refractive index of the film, $n_2$, is approximately related to the volumetric composition of the films, assuming the film structure to be heterogeneous on a scale less than the wavelength f light and with no regular repeating patterns.

For the dry film, $$n_2 \approx n_{Al_2O_3}(1-f_p)+f_p$$

where $n_{Al_2O_3}$ is the refractive index of alumina, $f_p$ is the pore fraction of the porous alumina and the refractive index of air is taken to be 1. As the pores of the alumina film fill with solution Equation 3 becomes:

$$n_2 \approx n_{Al_2O_3}(1-f_p)+1.33f_p$$

where the refractive index of the filling solution is assumed to be that of water. For any value of m, $$\frac{\lambda_{max,dry}}{\lambda_{max,wet}} = \frac{\sqrt{n_{2,dry}^2 - \sin^2(\theta_0)}}{\sqrt{n_{2,wet}^2 - \sin^2(\theta_0)}}$$

Since the refractive index of the solution filled film is always greater than that of the dry film, the filling of the pores will always result in a red shift.

Example 2

Reduction of Water

In a further aspect of the invention, experiments by specular reflectance spectroscopy on the ORTLE as a function of potential in a simple solution of 0.05 M $Na_2SO_4$ provided the following results. The exemplary embodiment described below is similar to the foregoing embodiment; therefore, those skilled in the art will refer to the previous embodiment for enabling descriptions of similar components, construction and operation of the ORTLE.

Figure 8:
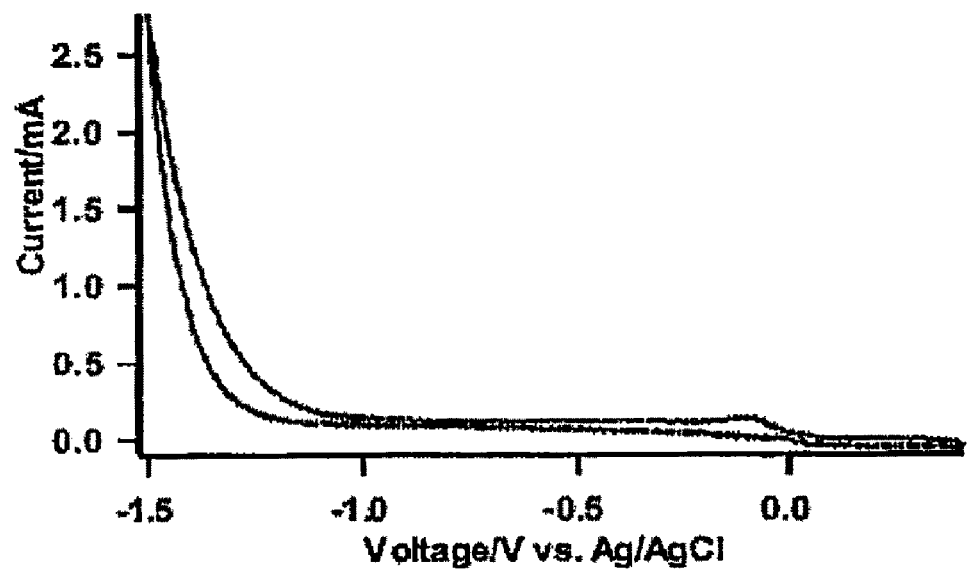
FIG. 8 is a graph showing a CV obtained for an ORTLE according to another aspect of the invention.

For these experiments, the auxiliary and reference electrodes 28, 30 as shown in FIG. 2 were inserted into the cell 20 and the three electrodes 10, 28, 30 were connected to the potentiostat (not shown). FIG. 8 shows a CV of the $Na_2SO_4$ solution where the potential was swept from +0.4V to -1.5V vs. (Ag/AgCl). The positive potential limit observed for the ORTLE 10 was apparently due to the gold oxide formation. More positive potentials resulted in delamination of the fragile gold film 16 from the porous alumina substrate 14, a common indicator of stress at a film/substrate interface 34. The negative potential limit of the ORTLE 10 was not due to delamination but apparently to dissolution of the porous alumina 14 by hydroxide ions generated during hydrogen evolution. The cathodic current associated with hydrogen evolution can be seen to begin at approximately -1.1V (vs. Af/AfCl) in FIG. 8.

Figure 9A:
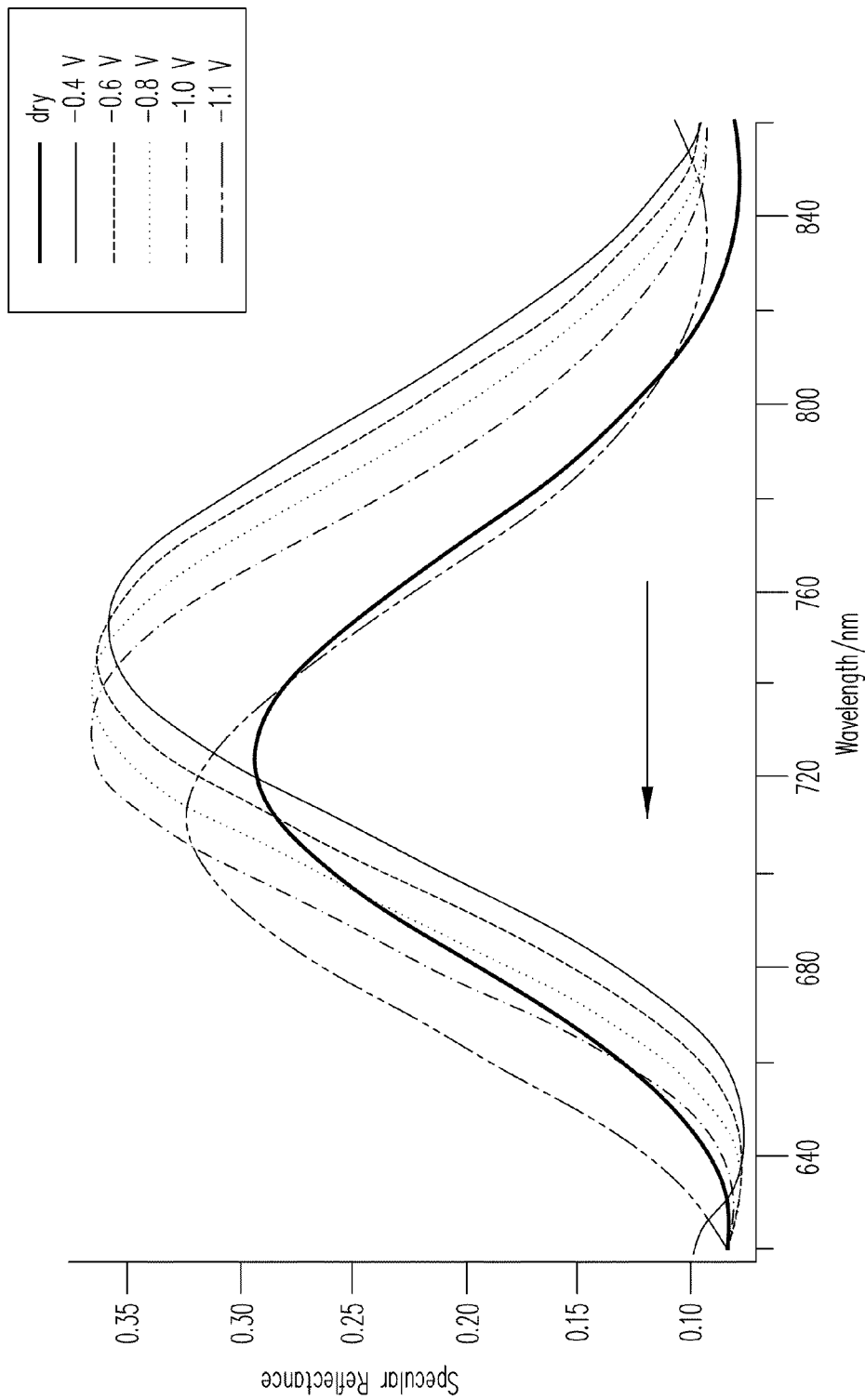
FIG. 9a is a graph showing an effect of potential on a specular reflectance spectrum concentrating on a peak at approximately 755 nm.

An ORTLE 10 for which results are depicted in FIG. 9A show a "dry" reflectance spectrum in which one of the observed peaks was centered at 725 nm. The addition of the sodium sulfate solution to the cell 20 caused this peak to shift to 755 nm. Reflectance spectra were acquired during the 400s that the potential was held at a certain value for steps to potentials between +0.1V and -1.2V (vs. Ag/AgCl). FIG. 9A shows detail in the reflectance spectrum of the ORTLE 10 at a subset of these potentials, between -0.4V and -1.1V (vs. Ag/AgCl), with the "dry" spectrum for reference. No significant changes were observed in the ORTLE reflectance spectra at potentials positive of -0.5V (vs. Ag/AgCl). When the potential was stepped to -0.5V (vs. Ag/AgCl), however, a blue shift of the peaks was observed. As FIG. 9A shows, the interference peak at 755 nm continued to shift toward the blue very gradually with increasing negative potential until -1.0V. A decrease in intensity was not observed over this potential range; in fact, a slight increase in intensity was observed.

When the potential was stepped to -1.1V, however, a more pronounced blue shift of the large peak at 755 nm was observed that was accompanied by a substantial decrease in intensity. This is interpreted as a result of gas infiltrating the pores of the alumina. Spectra obtained at more negative potentials showed weaker and broader interference peaks that did not recover when the electrode was returned to more positive potentials. This is interpreted as a result of the concomitant generation of hydroxide during hydrogen evolution. It is possible that the pH may be controlled with a buffer solution.

In electrochemical experiments carried out with ORTLEs outside of the spectrometer, it was not possible to see hydrogen evolution with the naked eye until the potential approached -1.5V. The increase in current observed in FIG. 8 near -1.1V is, however, attributable to the onset of water reduction. The low level of hydrogen production occurring at -1.1V was insufficient to form bubbles large enough to be observed by the naked eye, but sufficient to strongly perturb the ORTLE specular reflectance. Assuming pores to be filled initially with water and that this water is displaced by gaseous hydrogen generated at the electrode, the apparent refractive index of the film can be written as:

$$n_2 \approx n_{Al_2O_3}(1-f_p) + 1.33f_p - \frac{RTn_{H_2}}{3dA}$$

where $n_{H_2}$ is the number of moles of $H_2$ produced, A is the area of the electrode, R is the ideal gas constant, and T is the absolute temperature.

Inserting this definition into equation 2, solving for wavelength and taking the derivative with respect to the number of moles of $H_2$ produced under initial conditions of pores filled with only water or a water-like electrolyte, the following is obtained:

$$\lambda_{max} = \frac{2d\sqrt{(n_{Al_2O_3} - f_p(n_{Al_2O_3} - 1.33))^2 - \sin^2(\theta_0)}}{m}$$

$$\frac{\partial \lambda_{max}}{\partial n_{H_2}} = \frac{2RT(n_{Al_2O_3} - f_p(n_{Al_2O_3} - 1.33))}{3mA\sqrt{(n_{Al_2O_3} - f_p(n_{Al_2O_3} - 1.33))^2 - \sin^2(\theta_0)}}$$

Inserting a void fraction of 0.32 (estimated from ellipsometry), a film thickness d of 680 nm (estimated from modeling of the film in FIG. 6), and an incident angle of 45 degrees, the maxima should occur at:

$$\lambda_{max} \approx \frac{1851 \text{ nm}}{m}$$

From Equation 5, it is evident that m=2 for the long wavelength peak in FIG. 6, and m is 3, 4 and 5 for the peaks at progressively shorter wavelengths. Returning to Equation 4, the sensitivity of the peak position of the m=2 peak to hydrogen is:

$$\frac{\partial \lambda_{max}}{\partial n_{H_2}} = \frac{9 \times 10^{10} \text{ nm} \cdot \text{mol}^{-1} \cdot \text{cm}^2}{A}$$

Equation 6 indicates that 0.1 nanomole of $H_2$ produced per centimeter squared area of electrode surface could result in a 9 nanometer hypsochromic shift in the m=2 peak. Assuming that a 1 nm shift could be detected, and assuming the sensor on the end of a fiber-optic with an area of $10^{-4}$ cm, approximately 1 fM of $H_2$ evolution could be detected if the gas were captured in the pores of the alumina.

Figure 9B:
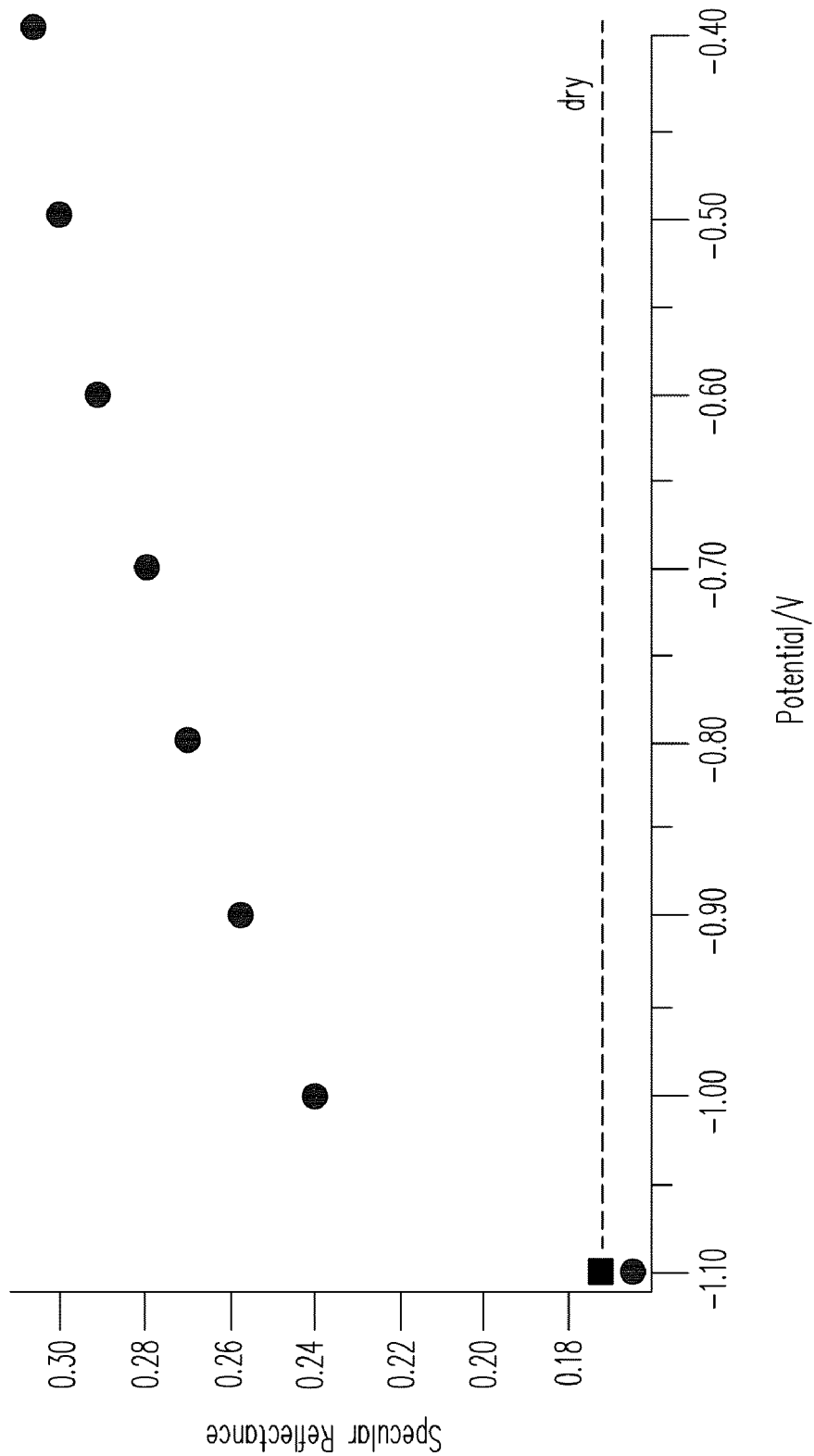
FIG. 9B shows a decrease in magnitude of the reflectance at 780 nm with increasing negative potential, particularly showing by dashed line a dry state of the ORTLE at 780 nm according to another aspect of the invention.

Subtle shifts in the wavelength of the interference peak maximum in FIG. 9A were observed at potentials as positive as −0.5V (vs. Ag/AgCl). The origin of this shift is unknown at present, but must involve changes in the composition of the porous film or of the solution in the pore volume. The blue shift indicates an overall decrease in the optical thickness of the film under these conditions, an effect that is consistent with displacement of pore solution by nanoscale bubbles. In FIG. 9B, the variation in the magnitude of the reflectance at 780 nm is plotted against potential. As shown, the intensity follows a similar trend with varying potential, in that a large increase of intensity is observed upon the addition of solution and a gradual decrease observed with increasing negative potential. Eventually, at −1.1V, FIG. 9B shows that the intensity is similar to that of the electrode in the dry state.

Conclusion

A thin layer film based on a gold-coated, porous alumina film, for example, has been shown and described. The thin layer film was placed in a cell and subjected to cyclic voltammetry and spectroscopic techniques and by spectroelectrochemistry in which a combination of specular reflectance spectroscopy and chronoamperometry was used. Typical spectra exhibited several strong interference peaks that resulted from the presence of a small amount of unanodized aluminum at the glass/porous alumina interface. A red shift of the peaks in the specular reflectance spectrum and an increase in intensity was observed upon the introduction of a sodium sulfate solution to the spectroelectrochemical cell where the ORTLE was mounted. This is likely due to refractive index changes arising from the filling of the pores by the solution. A blue shift of the peaks could be induced by stepping the potential to values increasingly negative of −0.5V (vs. Ag/AgCl) and towards the background limit of the solution. Upon stepping to −1.1V, a pronounced blue shift was observed, accompanied by a decrease in intensity. This is likely due to the production of hydrogen within the pores of the ORTLE.

The ORTLE differs from typical thin-layer electrodes in several ways. First, no transparent electrodes are required, and the solution does not have to be transparent or even homogenous, because the nanostructured electrode face filters out particles large enough to cause significant scattering. The electrode can thus be used in bulk solutions as a window that does not allow light into the bulk—similar to total internal reflection techniques, but with no critical angle constraints. Further, the electrode can potentially be designed to combine refractive-index measurements with surface plasmon resonance and UV-visible absorbance measurements with very minor changes. Moreover, while a top layer of the ORTLE can be a metal, the top layer is not limited to use as an electrode for spectroelectrochemical analysis. Additionally, while the interference pattern shifts described above indicate a change in the refractive index of the material filling the pores, measurements are not limited to interferometry but can include absorption properties of the fluid. Thus, one can also use the ORTLE to perform infrared or UV-visible spectroscopy measurements on the fluids in the pores to identify those fluids.

While preferred embodiments of the invention have been shown and described, those skilled in the art will recognize that other changes and modifications may be made to the foregoing examples without departing from the scope and spirit of the invention. It is intended to claim all such changes and modifications as fall within the scope of the appended claims and their equivalents. Moreover, references herein to "top," "bottom," "upward," "upper," "higher," "lower," "downward," "descending," "ascending," "side," "first," and "second" structures, elements, designations, geometries and the like are intended solely for purposes of providing an enabling disclosure and in no way suggest limitations regarding the operative orientation or order of the exemplary embodiments or any components thereof.

That which is claimed is:

1. A thin layer electrode disposed in a fluid in an atmosphere, the thin layer film comprising:
   a transparent base substrate;
   a thin film disposed on the base substrate, the thin film defining a plurality of pores therein; and
   a material disposed on the thin film such that the pores are exposed to an atmosphere, the material configured to isolate a portion of the fluid in the pores from the atmosphere when a potential is applied, the material further configured for reflectance of an incident light when the potential is applied to redirect into the pores at least a portion of the incident beam passing through the transparent base substrate into the pores in a direction of the material.

2. The thin layer electrode as in claim 1, wherein the transparent base substrate is glass.

3. The thin layer electrode as in claim 2, wherein the thin film is alumina exhibiting a depth of 250 nm to 1000 nm.

4. The thin layer electrode as in claim 1, wherein the material is a gold layer having a nanostructured face disposed away from the thin film and configured to filter scatter-causing particles suspended in the liquid or gaseous matter.

5. The thin layer electrode as in claim 1, wherein the fluid is selected from the group consisting of a ferricyanide, a sodium sulfate, a water, a gas, and combinations thereof.

6. The thin layer electrode of claim 1, wherein the reflectivity of an interface between the substrate and the film is comparable to a reflectivity of an interface between the film and the reflective material.

7. A thin layer apparatus for fluid analysis, the thin layer apparatus comprising:
   a transparent base substrate;
   a thin film sputtered on the base substrate, the thin film defining a plurality of pores therein, each of the pores having a diameter of 80 nm to about 100 nm and a depth of 250 nm to about 1000 nm, the pores configured to isolate a portion of a fluid from the atmosphere when immersed therein, and
   an electrode configured to provide a potential to the thin film,
   wherein the transparent substrate and the thin film are configured for reflectance of an incident light directed into the pores and passing through the transparent base substrate in a direction of the atmosphere when a potential is provided to the thin film.

8. The thin layer apparatus as in claim 7, further comprising a material disposed on the thin film such that the pores are in communication with the fluid, the material having a specular surface to reflect into the pores an incident beam entering the pores through the transparent base substrate in a direction of the material.

9. A method for analyzing matter comprising the steps of:
   (a) introducing a fluid into an optically reflective thin layer electrode, the electrode including a transparent base substrate with a porous layer formed thereon, and a reflective layer disposed on the porous layer, wherein a quantity of the fluid enters at least a pore in the porous layer;
(b) applying a potential to the reflective layer such that a portion of the quantity of fluid that has entered at least a pore is isolated from a remaining bulk of the fluid;
(c) directing a light to the optically reflective thin layer electrode;
(d) measuring a reflectance from a reflected light from the optically reflective thin electrode; and
(e) monitoring a wavelength for which a reflectance forms a peak.

10. The method of claim 9, wherein the applied potential is between +0.4 V to −1.5 V.

11. The method of claim 9, wherein the transparent base substrate is made of glass.

12. The method of claim 9, further comprising the step of holding the potential for 200 seconds to 400 seconds.

13. The method of claim 9, further comprising the step of directing the light at the base substrate at about a 45 degree angle from a direction normal to the reflective thin layer electrode.

* * * * *